(12) United States Patent
Federer et al.

(10) Patent No.: US 7,006,928 B2
(45) Date of Patent: Feb. 28, 2006

(54) DEVICE AND METHOD FOR DETERMINING THE STABILITY OF SUBSTANCES AND FORMULATIONS

(75) Inventors: Beat Federer, Zürich (CH); Markus Roggli, Möriken (CH); Martin Roth, Basel (CH)

(73) Assignee: RPD Tool AG, Muttenz (CH)

( * ) Notice: Subject to any disclaimer, the term of this patent is extended or adjusted under 35 U.S.C. 154(b) by 18 days.

(21) Appl. No.: 10/480,878

(22) PCT Filed: Jun. 8, 2002

(86) PCT No.: PCT/CH02/00300

§ 371 (c)(1),
(2), (4) Date: Dec. 12, 2003

(87) PCT Pub. No.: WO02/101363

PCT Pub. Date: Dec. 19, 2002

(65) Prior Publication Data

US 2004/0167724 A1    Aug. 26, 2004

(30) Foreign Application Priority Data

Jun. 13, 2001   (CH) .................................... 1082/01

(51) Int. Cl.
*G01N 35/02*   (2006.01)

(52) U.S. Cl. ............................ 702/30; 702/31; 702/32; 422/63; 700/266

(58) Field of Classification Search ............ 702/30–32; 422/631, 671, 102; 436/43, 47, 173; 700/266; 250/343

See application file for complete search history.

(56) References Cited

U.S. PATENT DOCUMENTS

| | | | | |
|---|---|---|---|---|
| 6,122,042 A | * | 9/2000 | Wunderman et al. | 356/73 |
| 6,730,517 B1 | * | 5/2004 | Koster et al. | 436/47 |
| 6,799,120 B1 | * | 9/2004 | Sepetov et al. | 702/19 |
| 2001/0053530 A1 | * | 12/2001 | Klein et al. | 435/7.1 |
| 2002/0009394 A1 | * | 1/2002 | Koster et al. | 422/65 |
| 2003/0056576 A1 | * | 3/2003 | Mansky | 73/61.41 |
| 2004/0071888 A1 | * | 4/2004 | Chondroudis et al. | 427/402 |
| 2004/0146434 A1 | * | 7/2004 | Kane et al. | 422/100 |
| 2004/0241044 A1 | * | 12/2004 | Mordekhay | 422/65 |

FOREIGN PATENT DOCUMENTS

| | | |
|---|---|---|
| JP | 2000-249654 | 9/2000 |
| WO | WO 01/09391 A | 2/2001 |

\* cited by examiner

*Primary Examiner*—Carol S. W. Tsai
(74) *Attorney, Agent, or Firm*—Speckman Law group PLLC

(57) ABSTRACT

The invention relates to a novel device for determining the physical and chemical stability of substances and formulations by means of samples. Said device is provided with a vibration spectrometer, a container (1) for storing the samples in controlled conditions, a robot (10) for transporting the samples between the vibration spectrometer (12) and the container, and a computer (13) for controlling the processes and for automatically storing and evaluating the spectra of the samples received by the vibration spectrometer.

12 Claims, 3 Drawing Sheets

DEVICE AND METHOD FOR DETERMINING THE STABILITY OF SUBSTANCES AND FORMULATIONS

FIELD OF THE INVENTION

The present invention relates to a device and a method for determining the physical and chemical stability of substances and formulations on the basis of spectral data which, with the aid of suitable vibration spectrometers (middle-infrared, near-infrared, Raman spectrometers), may be recorded non-destructively completely automatically in short time intervals (minutes, hours, days) from substances and formulations stored under controlled conditions (temperature and/or ambient humidity and/or light).

BACKGROUND OF THE INVENTION

Typically, physical and chemical stabilities of substances and formulations are determined in such a way that the substances and formulations are stored in controlled storage conditions for a long period of time. At the beginning of the storage period and time intervals (several weeks, months, years) during the storage, samples are taken from the stored substances and formulations, which are subsequently assayed in a laboratory using physical and chemical analyses (chromatographic, electrophoretic, wet-chemical, and physical methods). These methods have various disadvantages:

- The performance of the classical physical and chemical analyses typically requires a large outlay in time since, for example, complex sample preparations are necessary for chromatographic and electrophoretic analyses.
- To perform chromatographic analyses, it is typically necessary for reference material having a known content of the substances to be assayed to be present.
- The material taken from the stored substances and formulations for the analyses may no longer be used for further storage, since the samples are destroyed in most cases in the classical physical and chemical analyses.
- Because of the great complexity, the analyses may only be performed at long time intervals. In comparison to the present invention, it takes significantly longer to obtain conclusions about the stability of the stored substances and formulations from the experimental data.

For example, a device for determining types of adsorbates, in which an infrared spectrometer disperses a beam of radiation from a catalyst which a gas is subjected to for analysis in order to adsorb adsorbates thereon, is known from DE-A-197 44061. The spectrometer outputs spectral data, corresponding to a wave number of the beam of the radiation, to a computer which has reference data stored. The computer standardizes the spectral data and the reference data and then calculates a product of the standardized spectral data and the reference data. A function of the product in relation to the wave number is then differentiated in order to obtain a differential function. Then, a specific wave number is determined for which the differential function is equal to zero, so that the shared peak of the spectral data and the reference data at the specified wave number is determined precisely.

It is therefore an object of the present invention to provide a device and a method which confirm information about the physical and chemical stability of substances and formulations rapidly, without destruction to the substances and formulations.

SUMMARY OF THE INVENTION

The present invention provides a device for measuring the physical and chemical stability of samples of substances and formulations, which comprises a vibration spectrometer, a container for storing samples under controlled conditions, a transport robot for transporting the samples between the vibration spectrometer and the container, and a computer for controlling the sequence of sample movements, and for automatic storage and analysis of the spectra recorded by the spectrometer.

The present invention also provides a method for measuring the physical and chemical storage stability of substances and formulations. Vibrations spectra of samples of substances and formulations are recorded by the vibration spectrometer at regular time intervals. Each individual vibration spectrum of a sample is next indexed using a sample number, the storage conditions, and measurement time. The recorded and indexed vibration spectra are then stored in a computer as raw data. As soon as the number of stored spectra exceeds a predetermined threshold value, the raw data of each individual sample is analyzed by way of statistical data anaylsis.

BRIEF DESCRIPTIONS OF THE DRAWINGS

Further advantages and embodiments of the present invention are explained in the following description with reference to the attached drawings, wherein.

DETAILED DESCRIPTION OF THE INVENTION

Figure 1:
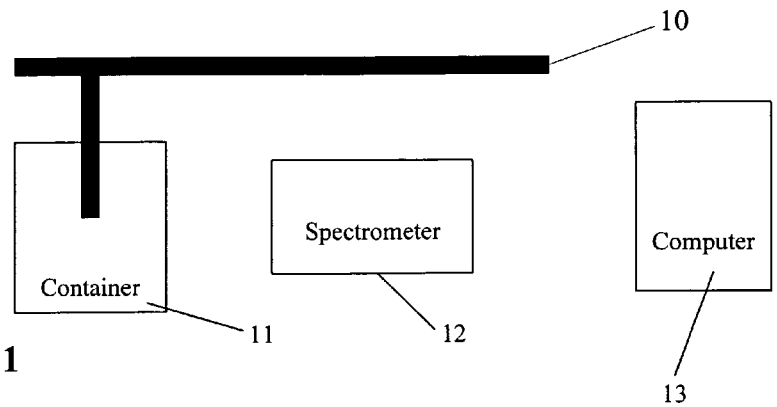
FIG. 1 shows a schematic illustration of a measurement device of the present invention.

FIG. 1 shows a schematic of a transport robot 10, commonly known in chemical laboratories, which may be moved back and forth between a storage container 11 and a spectrometer 12 by means of a computer 13. Samples of substance and formulations are transported by the transport robot 10 in a sample vessel (not shown) from the storage container 11 to the spectrometer 12, where the spectra are recorded. Subsequently, the robot 10 transports the samples back to the storage container 11. The movement sequences are programmed in the computer 13 so that the measurements are performed under the same measurement conditions (temperature, incident light, relative humidity).

To perform physical and chemical stability studies, in the method described here, vibration spectra from a sample of the substance or formulation stored in defined storage conditions are recorded automatically under identical measurement conditions using the spectrometer 12 in regular time intervals (minutes, hours, days). Middle-infrared, near-infrared, and Raman spectroscopy are vibration spectroscopy methods suitable for these studies. The recorded spectra of each sample are stored in the computer 13 as raw data, each spectrum being provided with the sample number, the storage conditions, and the time of the measurement using an index. The analysis of the raw data is performed through statistical data analysis. It begins for each sample automatically as soon as the number of spectra stored on the computer 13 is sufficient for a reasonable analysis and is recalculated as soon as new spectra of the sample are recorded. The current results of the analysis may be accessed at any time.

Figure 2:
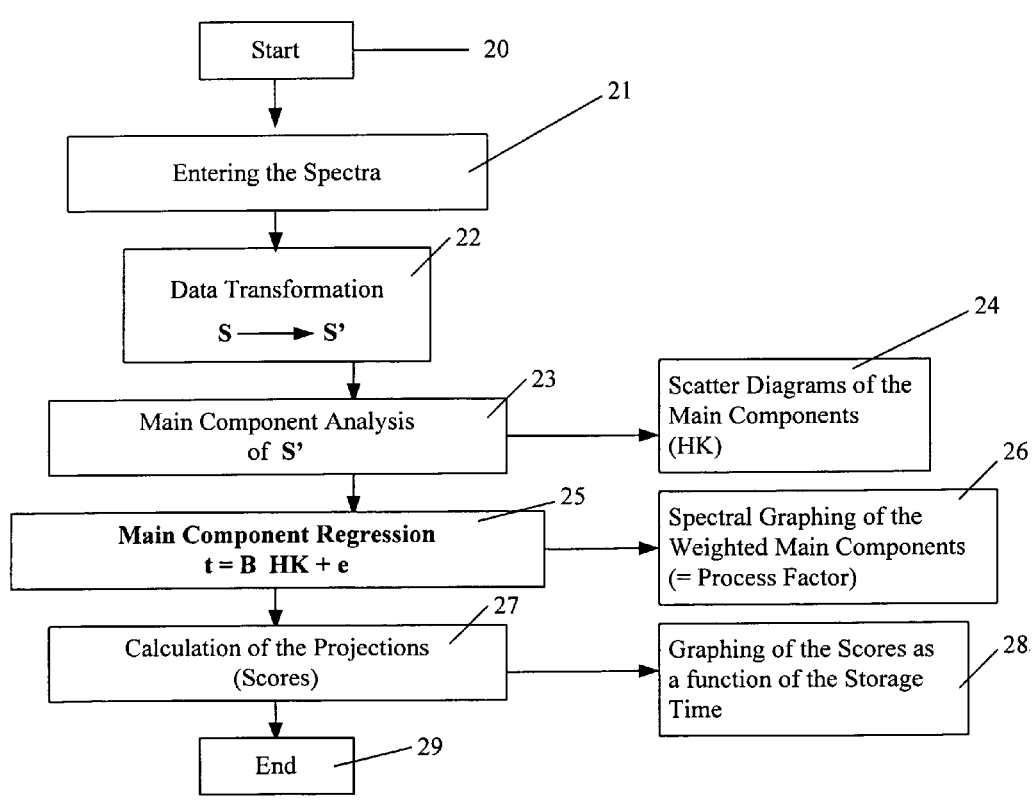
FIG. 2 shows a flowchart of the analysis preformed by the device of FIG. 1.

The execution of the automatic data analysis occurs according to the method indicated in the scheme in FIG. 2. At the start 20, the measurement is initiated by the computer 13. The first step 21 includes producing a data set which includes all spectra S of a sample at specific storage conditions, according to which a vector S is produced from the spectra entered in the computer 13. In step 22, a data transformation S→S' is then performed, by subtracting a baseline from each spectrum in the vector S, for example. The analysis begins with the spectra of the data transformation of all spectra in the data set which contain a baseline correction or a vector standardization, for example. The second analysis step 23 includes the analysis of the main components or similar transformations of all transformed spectra S' of a sample. The scatter diagram 24 of the main components may be graphed from this. With the aid of at least one of the calculated main components and the time of the measurement of each spectrum, the systematic temporal change of the spectra is subsequently determined with the aid of a regression calculation 25 of the main components in accordance with the formula $t=B*HK+e$, t being the vector from the storage time, B being the vector having the regression coefficients, HK being the matrix having the main components, and e being the vector having the experimental errors. The spectral representation 26 of the sums of the main components HK weighted with the regression coefficients then results therefrom. The results obtained from the regression calculation allow qualitative and quantitative statements about the physical and chemical stability of the sample. The projections or scores may be calculated (step 27) from the main component regressions 25, from which the scores may be graphed as a function of the storage time (step 28). After the calculation of the scores, the method is ended at step 29 and the measurements are continued on the next sample.

Figure 3:
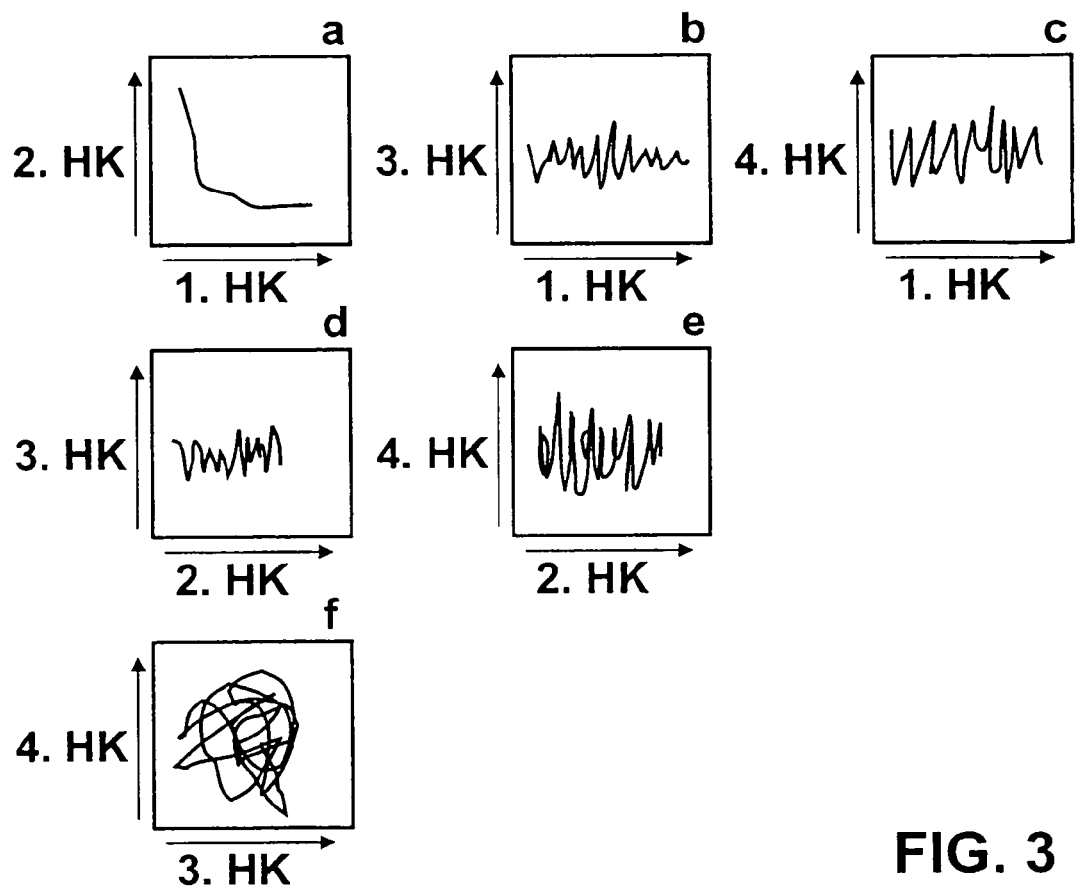
FIG. 3 shows a scatter diagram of main components of the device of FIG. 1.

In FIG. 3, the various main components 1.HK, 2.HK, 3.HK, and 4.HK are represented in the form of a scatter diagram in each case. These allow conclusions about the number of independent processes occurring during the storage of the sample. In this case, the individual spectra are represented in the diagrams as points which are connected in temporal sequence using a line. Particulars may be inferred from the book "Statische Datenanalyse-Eine Einfuhrung fur Naturwissenschaftler [Statistical Data Analysis—an Introduction for Physical Scientists]" by Werner A. Stahel, Vieweg 1995, about the main components on pp. 307 and 308, about scatter diagrams in chapter 3.1, particularly pp. 34 to 36, and about the matrix of scatter diagrams in chapter 3.6, pp. 48 to 51.

Figure 4:
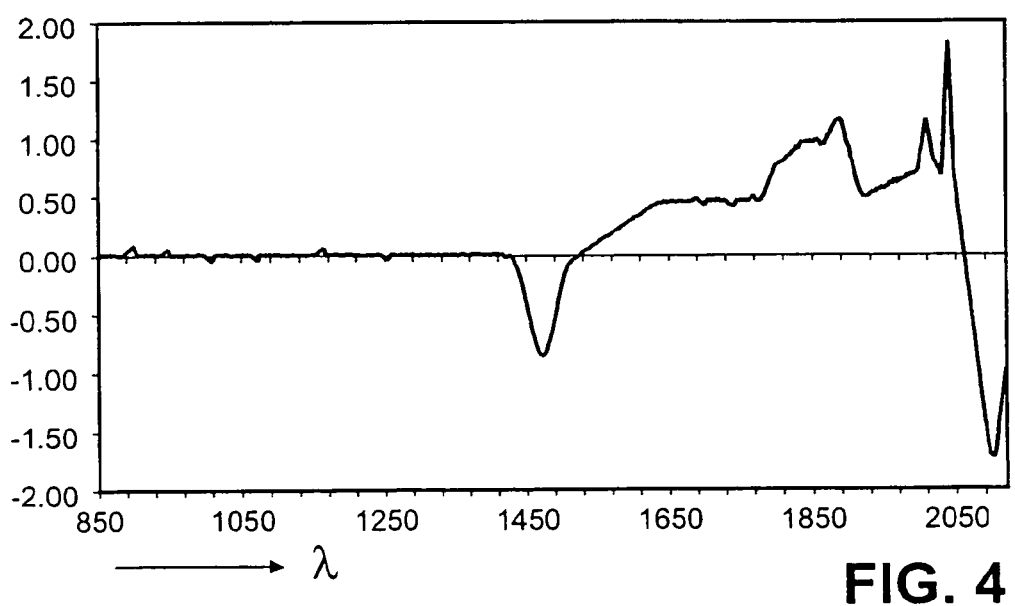
FIG. 4 shows a diagram of the main components of FIG. 3, weighted with the coefficients of the regression calculation.

A diagram of the sum of the main components (or process factors) weighted with the coefficients of the regression calculation is shown in FIG. 4. The wavelength λ is plotted on the x-axis, the y-axis is dimensionless and shows the intensity changes. At a wavelength of approximately 1450 nm, there is a significant decrease of the intensity, from which a decrease of the concentration of the vibration oscillations of the associated molecule, and therefore reduced storability, may be concluded. The main components weighted with the coefficients of the regression calculation thus show the base vector for the temporal drift of the spectra and have the same physical units as these. The process factor allows conclusions to identify the materials participating in the physical and chemical alteration processes.

Figure 5:
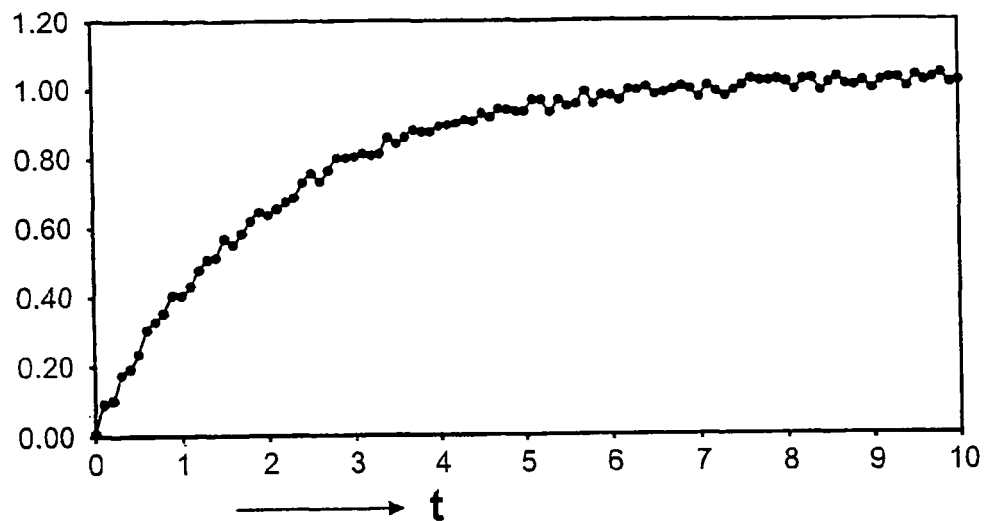
FIG. 5 shows a diagram illustrating the alteration from the scores.

The associated scores are obtained through mathematical projection of the transformed spectra onto the calculated process factor. The scores are shown in the temporal sequence in FIG. 5. Together with the time t of the measurement of the spectra, they allow conclusions about the kinetics of the physical or chemical alteration processes. In connection with the Lambert-Beer law, the extent of the alteration (e.g., the chemical degradation) may be established quantitatively from the scores, if the process may be uniquely assigned to a substance present in the sample from the associated loadings.

Figure 6:
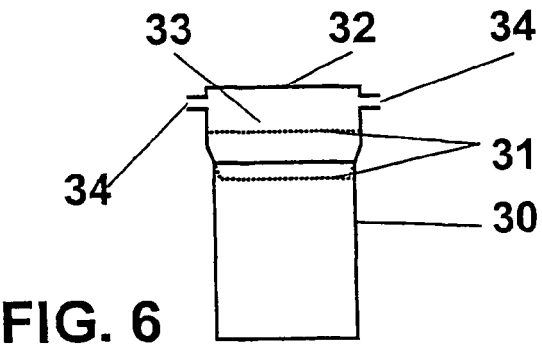
FIG. 6 shows a front view of a sample container having an evaporation device.
Figure 6A:
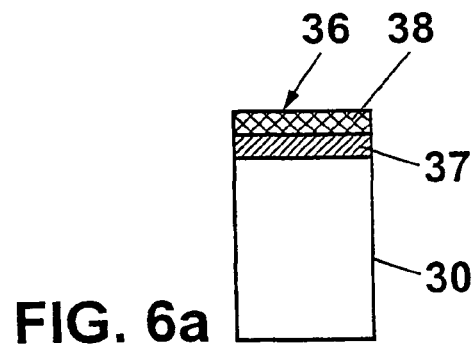
FIG. 6A shows a hermetically sealed sample container.

A sample vessel 30 having a cover 32 tightly sealed by seals 31 is shown in FIG. 6. An overflow Channel 33 is provided in the cover 32, which is connected on two diametrically opposite sides to hoses (not shown here) via connections 34. Using this sample vessel, the samples may be vaporized in a controlled way. For this purpose, the sample vessel 30 is sealed using the cover 32 after pouring in the sample liquid and the hoses are connected. The overflow channel 33 then has a protective gas flow over it in a regulated and/or constant gas flow during the storage and/or the evaporation of the solvent. The measurements of the vibration spectra then occur in the sample vessel 30. In addition, the sample vessel 30 may also be sealed hermetically using a suitable seal 36 (see FIG. 6a), which includes a mechanical closure 37 (e.g., stopper or twist closure) and an artificial resin layer 38, poured over it and cured, which hermetically seals the closure 37.

Figure 7:
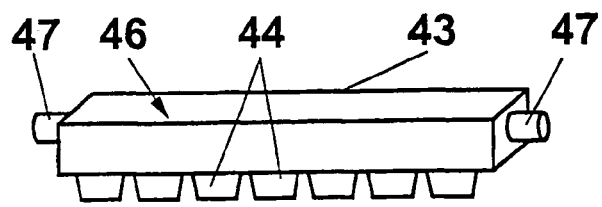
FIG. 7 shows a sample vessel having multiple depressions and an evaporation device for multiple sample containers.
Figure 7:
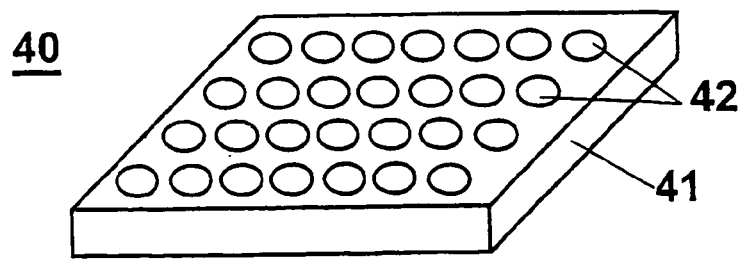

A further embodiment of a sample vessel 40 is illustrated in FIG. 7, which includes a microtest plate 41 having multiple depressions 42 and an evaporation device 43. The evaporation device 43 is provided with multiple cover-like caps 44 and an overflow channel 46 having connections 47. Such a microtest plate 41 is preferably made of quartz glass and is described, for example, in the catalog 66/97-1 of HELLMA GmbH & Co. D-79371 Mullheim, on page 155. The microtest plate 41 is sealed line by line with the evaporation device 43, acting as a cover. The overflow channel 46 subsequently has a protective gas flow over it at a regulated and/or constant gas flow during the storage and/or the evaporation of the solvent, which flows via hoses (not shown in the figures) connected to the connections 47. The measurement of the vibration spectra (NIR, Raman) occurs in the particular depression from below and/or, after the complete evaporation of the solvent and the removal of the evaporation device 43, from top to bottom in the transmission mode, or using an infrared and/or Raman microscope.

We claim:

1. A device for measuring the physical and chemical stability of a substance or formulation, comprising:
   (a) a vibration spectrometer for obtaining spectra of at least one sample of the substance or formulation at defined time intervals and under the same measuring conditions;
   (b) a storage container for storing the sample under controlled storage conditions between the defined time intervals, wherein the storage container comprises a means for observing the controlled storage conditions;

(c) a transport robot for transporting the sample between the vibration spectrometer and the storage container;

(d) a computer which controls sequences of sample movements, wherein the computer comprises a control unit with recording means for recording the spectra of the sample;

(e) a storage means for automatically storing the spectra of the sample; and (f) an evaluation means for evaluating the stored vibration spectra by means of statistical data analysis thereby determining the physical and chemical stability of the sample.

2. The device according to claim 1, wherein the vibration spectrometer is selected from the group consisting of: middle-infrared spectrometers, near-infrared spectrometers, and Raman spectrometers.

3. The device according to claim 1, wherein the container comprises at least one sensor for measuring and maintaining the controlled storage conditions.

4. The device according to claim 3, wherein the at least one sensor is selected from the group consisting of: light sensors, temperature sensors, humidity sensors, and sensors for measuring the gas atmosphere in the container.

5. The device according to claim 1, wherein the container further comprises an evaporation device having an overflow channel whereby the sample may be vaporized under controlled conditions.

6. The device according to claim 1, wherein the container is hermetically sealed by a seal.

7. The device according to claim 6, wherein the seal comprises a mechanical closure and an artificial resin layer which seals the closure.

8. A method for measuring the physical and chemical storage stability of a substance or formulation, comprising:

(a) storing at least one sample of the substance or formulation under controlled conditions;

(b) recording vibration spectra of the sample at regular time intervals and under the same measuring conditions;

(c) indexing each individual vibration spectrum of a sample with a sample number, storage conditions, and measurement time;

(d) storing the recorded and indexed vibration spectra in a computer as raw data; and (e) analyzing the raw data of each individual sample by statistical data analysis when the number of stored vibration spectra exceeds a predetermined threshold value, thereby determining the physical and chemical storage stability of the substance or formulation.

9. The method according to claim 8, wherein a data set is produced from all the spectra of an individual sample, and wherein the spectra are analyzed by data transformation in the data set.

10. The method according to claim 9, wherein the data transformation comprises a baseline correction.

11. The method according to claim 9, wherein the data transformation comprises a vector standardization.

12. The method according to claim 8, wherein all transformed spectra of an individual sample are analyzed by a main component analysis, and wherein a systematic temporal alteration of the spectra is established by regression calculation of the main components.

* * * * *